United States Patent [19]
Uhrberg

[11] Patent Number: 6,047,217
[45] Date of Patent: Apr. 4, 2000

[54] CARDIAC LEAD WITH IMPROVED POLYMER-TO-METAL JOINT

[75] Inventor: Anders S. Uhrberg, Angleton, Tex.

[73] Assignee: Intermedics Inc., Angleton, Tex.

[21] Appl. No.: 09/007,876

[22] Filed: Jan. 15, 1998

[51] Int. Cl.[7] .................................................. A61N 1/05
[52] U.S. Cl. ...................... 607/119; 607/122; 600/372; 600/374
[58] Field of Search .................................. 607/119, 122; 600/372, 374

[56] References Cited

U.S. PATENT DOCUMENTS

| | | |
|---|---|---|
| 4,236,525 | 12/1980 | Sluetz et al. . |
| 4,365,639 | 12/1982 | Goldreyer ............................ 607/122 |
| 4,662,382 | 5/1987 | Sluetz et al. . |
| 4,832,048 | 5/1989 | Cohen . |
| 4,858,623 | 8/1989 | Bradshaw et al. . |
| 4,913,164 | 4/1990 | Greene et al. . |
| 4,924,881 | 5/1990 | Brewer . |
| 4,967,766 | 11/1990 | Bradshaw . |
| 5,056,516 | 10/1991 | Spehr . |
| 5,129,404 | 7/1992 | Spehr et al. . |
| 5,545,188 | 8/1996 | Bradshaw et al. . |
| 5,593,433 | 1/1997 | Spehr et al. . |
| 5,645,580 | 7/1997 | Moaddeb et al. . |
| 5,713,945 | 2/1998 | Fischer et al. . |
| 5,735,891 | 4/1998 | White . |
| 5,755,762 | 5/1998 | Bush ....................................... 607/126 |

*Primary Examiner*—William E. Kamm
*Assistant Examiner*—Carl H. Layno
*Attorney, Agent, or Firm*—Schwegman, Lundberg Woessner & Kluth, P.A.

[57] ABSTRACT

A cardiac lead joint assembly is provided for connecting a polymeric sleeve to a tubular metallic structure, such as the tubular metallic connector that connects to the header of a cardiac stimulator. The joint assembly includes a tubular metallic member, which may be the tubular connector, an electrode, or some other structure in the lead. The tubular metallic member has an annular groove formed on the exterior surface thereof. A polymeric annular member is disposed around the tubular metallic member and is seated in the annular groove. The polymeric sleeve is disposed over a portion of the tubular metallic member and is secured to the polymeric annular member by an adhesive. The joint assembly provides a polymer-to-polymer interface for adhesive bonding.

25 Claims, 2 Drawing Sheets

CARDIAC LEAD WITH IMPROVED POLYMER-TO-METAL JOINT

BACKGROUND OF THE INVENTION

1. Field of the Invention

This invention relates generally to cardiac stimulator leads, and more particularly to method and apparatus for joining a polymeric sleeve to a tubular structure in a cardiac lead.

2. Description of the Related Art

Conventional implantable cardiac stimulator systems consist of a cardiac stimulator and one or more elongated tubular leads. The cardiac stimulator is ordinarily encased within a metallic can. The proximal ends of the leads are connected physically and electrically to the cardiac stimulator via a structure commonly known as a header. The distal end of the lead is implanted near the tissue site requiring electrical stimulation or sensing. The lead functions to carry electrical signals from the cardiac stimulator to the targeted tissue and signals from the targeted tissue back to the cardiac stimulator. The cardiac stimulator may be a pacemaker, a defibrillator, a sensing instrument, or some combination thereof.

There is great variability in the structure of conventional cardiac leads. Although some of this variety can be traced to differences in the design methodology of various lead manufacturers, many of the structural differences are simply a result of the many different types of arrhythmia therapy now possible through cardiac stimulation, such as multi-chamber pacing, defibrillation, and coronary sinus pacing, among others. However, despite the many differences in the designs of various cardiac leads, most such leads share several common structural features.

The proximal end of a typical cardiac lead, such as a bipolar lead, consists of a tubular metallic connector that is adapted to be secured to the header of a cardiac stimulator. The distal end of the lead includes one or more tubular structures that are often metallic, and may serve not only as electrodes, but may also include mechanisms to secure the lead to the targeted tissue. Electrical pathways between the proximal connector and the distal electrodes are established by one or more conductor wires extending between the proximal connector and the distal electrodes. The proximal connector and the distal electrodes are physically connected by a tubular insulating sleeve that not only physically connects the two ends of the lead, but also functions to electrically insulate the conductor wires of the lead from invasion by body fluids and tissues. Bipolar leads that incorporate non-insulated conductor wires usually include two insulating sleeves that are concentrically disposed. One of the conductor wires is disposed inside the innermost sleeve and the other wire is disposed between the first sleeve and the second sleeve.

The attachment of the sleeve(s) to the tubular structures of the proximal connector and the electrode requires a bonding between dissimilar materials, namely, the polymer sleeve to the metallic tubular structures. In conventional leads, the outer surface of the tubular structure(s) and the inner surface of the sleeve(s) are both relatively smooth. The bonding of the mating smooth surfaces is accomplished by application of a biocompatible medical grade adhesive between the surfaces. The adhesive bond is the primary mechanism to prevent the sleeve(s) from separating from the metallic tubular structures.

There are several disadvantages associated with the interconnection between the insulating sleeve and the metallic structures in conventional cardiac leads. The strength of the adhesive bond between the tubular metallic structure and the sleeve is dictated in large part by the strength of the adhesive agent, and the initial conditions of the exterior of the tubular structure and the interior of the insulating sleeve. Surface contaminants on the exterior of the tubular structure or the interior of the insulating sleeve may prevent the adhesive from bonding properly, and result in a weakened joint. To avoid or reduce the risk of improper bonding due to contamination, costly surface preparation procedures must normally be undertaken prior to application of the adhesive. In a commonly followed procedure, the metallic tubular structure is washed thoroughly in a mixture of isopropyl alcohol and heptane. Although immersion of the tubular structure in the cleaning agent is sometimes sufficient to adequately clean the structure, physical scrubbing by brushing or use of some other tool is often necessary to achieve an acceptable level of surface purity. The cleaning process slows manufacturing, requires the labor intensive input of skilled manufacturing workers, and employs solvents that often require specialized air handling equipment.

This invention is directed to overcoming or reducing one or more of the foregoing disadvantages.

SUMMARY OF THE INVENTION

In accordance with one aspect of the present invention, a cardiac lead connector assembly is provided. The cardiac lead connector assembly includes a tubular metallic member that has an annular groove formed on the exterior surface thereof. A polymeric annular member is disposed around the tubular metallic member and is seated in the annular groove. A polymeric sleeve is disposed over a portion of the tubular member and over the polymeric annular member. A portion of the polymeric sleeve proximate the polymeric annular member is diametrically stretched by the polymeric annular member. The polymeric sleeve is retained on the tubular member by interaction between the polymeric annular member and the polymeric sleeve.

In accordance with another aspect of the present invention, a cardiac lead connector assembly is provided. The cardiac lead connector assembly includes a tubular metallic member that has an annular groove formed in the exterior surface thereof. A polymeric sleeve is disposed over a portion of the tubular metallic member and the annular groove. The interior surface of the polymeric sleeve has an inwardly projecting annular member that is seated in the annular groove.

In accordance with still another aspect of the present invention, a method of attaching a polymeric sleeve to a tubular member of a cardiac lead where the tubular member has an annular groove formed in the exterior thereof is provided. The method includes the step of slipping a polymeric annular member over the tubular member and seating the polymeric annular member in the annular groove. An adhesive is applied to the exterior of the polymeric annular member. The polymeric sleeve is slipped over the tubular member whereby the sleeve covers the polymeric annular member and whereby the adhesive bonds the exterior of the polymeric annular member to the interior of the polymeric sleeve.

In accordance with still another aspect of the present invention, a method of attaching a polymeric sleeve to a tubular member of a cardiac lead where the tubular member has an annular groove formed in the exterior thereof is provided. The method includes the steps of slipping a polymeric annular member over the tubular member and seating the polymeric annular member in the annular groove. The polymeric sleeve is slipped over the tubular member whereby the sleeve covers the polymeric annular member and whereby the exterior of polymeric annular member adheres to the interior of the polymeric sleeve.

In accordance with yet another aspect of the present invention, a cardiac lead is provided. The cardiac lead includes a tubular electrode coupled to the distal end of the polymeric sleeve for passing electrical signals to and from heart tissue. The tubular electrode has an annular groove formed on the exterior surface thereof. A polymeric annular member is disposed around the tubular electrode and is seated in the annular groove. A polymeric sleeve is provided that has a proximal end and a distal end disposed over a portion of the polymeric annular member and the tubular electrode and is secured to the polymeric annular member by an adhesive. A tubular metallic connector is coupled to the proximal end of the polymeric sleeve for connecting the lead to a cardiac stimulator.

In accordance with still another aspect of the present invention, a cardiac lead is provided. The cardiac lead includes a tubular electrode coupled to the distal end of the polymeric sleeve for passing electrical signals to and from heart tissue. The tubular electrode has an annular groove formed on the exterior surface thereof. A polymeric annular member is disposed around the tubular electrode and seated in the annular groove. The polymeric annular member is composed of a first polymeric material. A polymeric sleeve is provided that has a proximal end and a distal end disposed over a portion of the polymeric annular member and the tubular electrode. The polymeric sleeve is composed of a second polymeric material. The first and second polymeric materials exhibit adhesive properties. A tubular metallic connector is coupled to the proximal end of the polymeric sleeve for connecting the lead to a cardiac stimulator.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
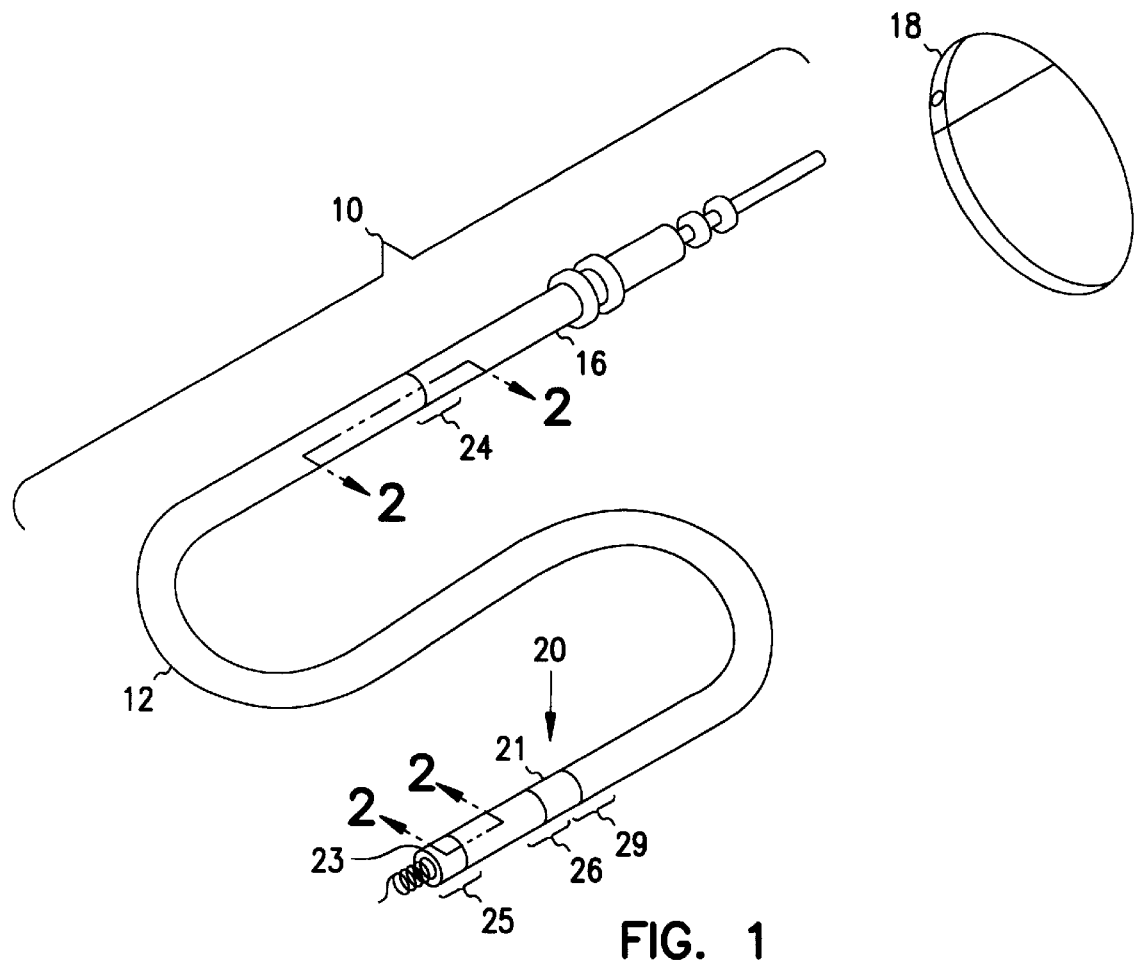
FIG. 1 is a pictorial view of an exemplary embodiment of a cardiac lead in accordance with the present invention.

In the drawings described below, reference numerals are generally repeated where identical elements appear in more than one figure. Turning now to the drawings, and in particular to FIG. 1, there is shown an exemplary cardiac lead 10 that may be suitable for either endocardial or epicardial fixation to a human heart (not shown). The lead assembly 10 includes a flexible polymer insulating sleeve 12 that is coupled proximally to a connector 16. The connector 16 is designed to be inserted into a cardiac stimulator 18, and is shown highly exaggerated in size relative to the cardiac stimulator 18. The cardiac stimulator 18 may be a pacemaker, a cardioverter/defibrillator, or other type of stimulator or a sensing instrument. The illustrated embodiment of the lead 10 is bipolar. Accordingly, the distal end 20 of the sleeve 12 includes two electrodes, an annular electrode 21, and a tip electrode 23 disposed distal to the annular electrode 21. One or more conductors 29 (FIG. 2) electrically connect the connector 16 and the electrodes 21, 23.

The connector 16 and the tip electrode 23 are tubular metallic members composed of titanium, stainless steel, or like biocompatible metallic materials. The skilled artisan will appreciate that the term "tubular" may encompass a variety of hollow or solid cylindrical or tubular like members. The union of the sleeve 12 to the connector 16, the annular electrode 21, the tip electrode 23 is provided by cardiac lead joint assemblies, denoted generally at 24, 25, 26, and 27 (hereinafter "joint assembly or joint assemblies"). The detailed structure of the joint assembly 25 is illustrative of the structure of the joint assemblies 24, 26, and 27, and may be understood by referring now also to FIG. 2, which is a cross-sectional view of FIG. 1 taken at section 2—2. The proximal end 28 of the electrode 23 terminates in a reduced diameter portion 30, thereby defining an annular shoulder 32. The distal end 34 of the sleeve 12 is slipped over the reduced diameter portion 30 and abuts the annular shoulder 32. The reduced diameter portion 30 is provided with an annular groove 36. A polymeric annular member or bridge 38 is seated snugly in the annular groove 36. The bridge 38 is secured to the reduced diameter portion 30 by interference. To provide this interference fit, the bridge 38 is fabricated with an unstretched inner diameter that is slightly smaller than the diameter of the reduced diameter portion 30 at the base of the annular groove 36.

The bridge 38 has a generally toroidal shape and an elliptical cross-section. The skilled artisan will appreciate that the term "elliptical" may encompass circular cross-sections. The annular groove 36 has a corresponding concave cross-section to accommodate the rounded outer surface of the bridge 38. As discussed below, the bridge 38 and the annular groove 36 may be fabricated with other types of cross-sections.

The sleeve 12 may be composed of a biocompatible flexible insulating polymeric material, such as silicone, polyurethane or like materials. The bridge 38 may be composed of the same types of materials used to fabricate the sleeve 12.

Application of the bridge 38 to the annular groove 36 requires temporary stretching of the bridge 38 to an increased diameter so that the bridge 38 may be slipped over the reduced diameter portion 30 and seated in the annular groove 36. This stretching step may be accomplished by mechanically expanding the bridge 38 or by swelling the bridge 38 in a chemical bath of heptane or other suitable swelling solvent and allowing the bridge 38 to dry and return to its original size after placement in the groove 36. In addition to relying on interference to secure the bridge 38 to the reduced diameter portion 30, a suitable medical grade adhesive, such as commonly available silicone-based adhesive or like adhesives, may be applied to the annular groove 36 prior to seating the bridge 38.

Application of the distal end 34 of the sleeve 12 over the reduced diameter portion 30 and the bridge 38 may require temporary stretching of the distal end 34 in the same manner as described above for the bridge 38. The distal end 34 of the sleeve 12 is provided with an unstretched inner diameter that is slightly smaller than the outer diameter of the bridge 38. Following application of the sleeve 12 over the reduced diameter portion 30 and the bridge 38, the sleeve 12 will be diametrically stretched proximate the bridge 38. The localized diametric stretching of the sleeve 12 gives rise to various interactions between the sleeve 12 and the bridge 38 that provide resistance to relative longitudinal movement between the sleeve 12 and the reduced diameter portion 30. First, the interference fit produces static friction between the inner surface of the distal end 34 and the bridge 38. Second, the sleeve 12 will contract diametrically at the proximal and distal sides of the bridge 38. The diametric contractions produce, in effect, annular shoulders in the inner surface of the distal end 34 proximally and distally to the bridge 38 that engage the proximal and distal sides of the bridge 38 and thereby resist relative longitudinal movement between the sleeve 12 and the reduced diameter portion 30.

Certain types of materials, such as silicone, exhibit inherent adhesive properties. Accordingly, where the sleeve 12 and the bridge 38 are both composed of silicone or other materials exhibiting adhesive properties, the adhesive interaction between the mating surfaces of the distal end 34 of the sleeve 12 and the bridge 38 may provide another type of interaction to resist relative longitudinal movement of the sleeve 12 and the reduced diameter portion 30.

In addition to relying on the aforementioned interactions to retain the sleeve 12 in position, the inner surface of the distal end 34 may be secured to the outer surface of the bridge 38 by application of a suitable biocompatible medical grade adhesive, of the type described above, to the outer surface of the bridge 38. The bridge 38 provides a polymer-to-polymer interface for adhesively bonding the inner surface of the distal end 34 to the reduced diameter portion 30. The medical grade adhesive will readily wet to the mating polymer surfaces of the distal end 34 and the bridge 38 to form a secure bond without the need for rigorous pre-cleaning with solvents and scrubbing. The same adhesive may also be applied to the interface between the interior surface of the distal end 34 and the exterior surface of the reduced diameter portion 30 on either side of the annular groove 36.

In contrast to the disclosed embodiment, the exterior surface of a reduced diameter portion and the mating interior surface of a sleeve in a conventional tubular connector are both relatively smooth, and the entire interface between the mating surfaces is polymer-to-metal. The adhesive bond formed by the medical grade adhesive between the mating surfaces of the reduced diameter portion and the sleeve must withstand the longitudinal shearing forces applied to the lead in order to prevent the sleeve from separating from the tubular metallic connector. As noted above, rigorous cleansing of the outer surface of the reduced diameter portion is necessary to eliminate contaminants which might adversely impact the strength and integrity of the bond.

Figure 2:
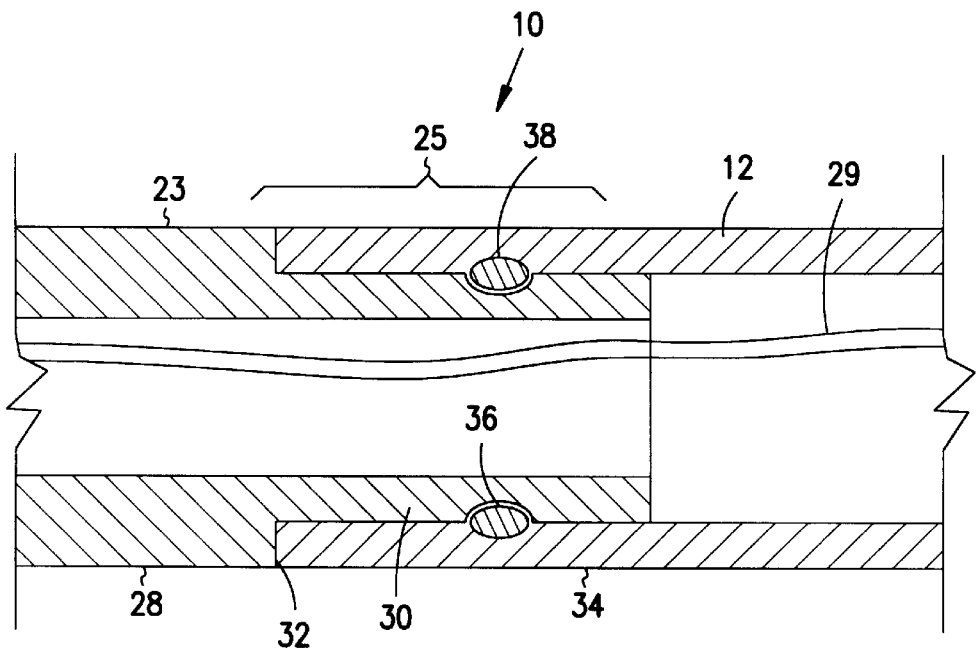
FIG. 2 is a cross-sectional view of FIG. 1 taken at section 2—2 and showing an exemplary cardiac lead joint assembly in accordance with the present invention.
Figure 3:
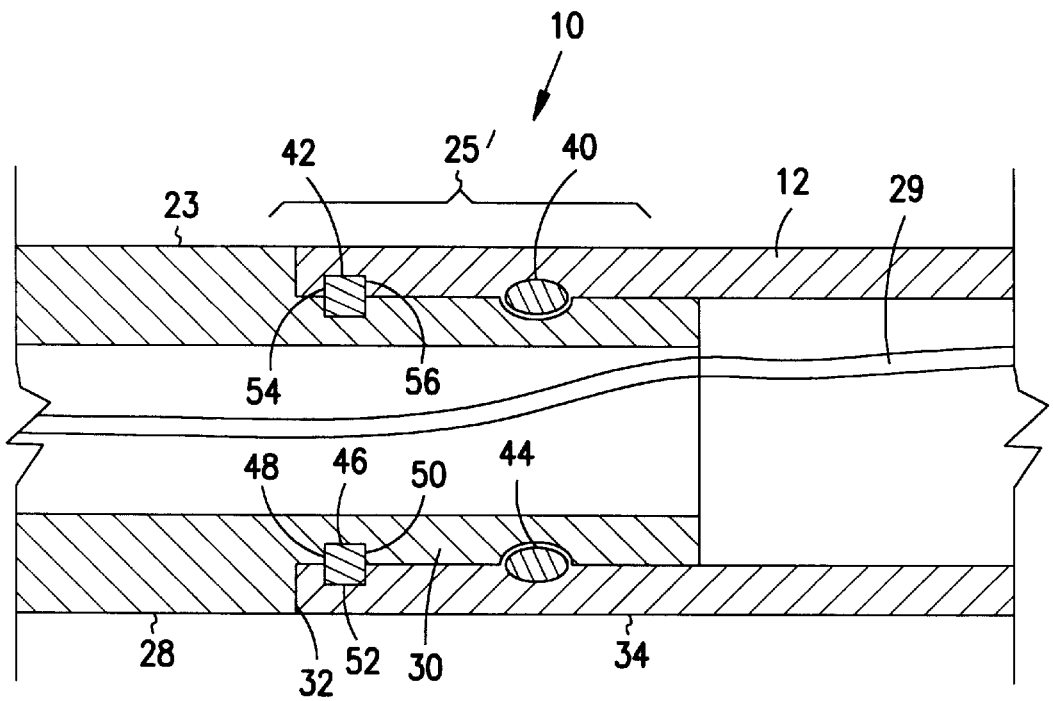
FIG. 3 is a cross-sectional view like FIG. 2 showing an alternate embodiment of a cardiac lead joint assembly in accordance with the present invention.

FIG. 3 depicts an alternate embodiment of the joint assembly, now designated 25'. FIG. 3 depicts the same general cross-sectional view as FIG. 2. In this embodiment, the joint assembly 25' is provided with two annular bridges 40 and 42 that are longitudinally spaced apart. The bridge 40 is identical to be above described bridge 38 (See FIG. 1) and is seated in an annular groove 44 identical to the aforementioned groove 36 (See FIG. 1). Like the bridge 40, the bridge 42 has a generally overall annular shape and is secured to the distal end 34 by a suitable medical grade adhesive. However, the bridge 42 is formed with a rectangular cross-section. The outer surface of the reduced diameter portion 30 has an annular groove 46 that is provided with a corresponding rectangular cross-section to enable the inner portion of the bridge 42 to seat snugly therein. The annular groove 46 has two opposing annular shoulders 48 and 50 which abut against opposite sides of the inner portion of the bridge 42. The inner surface of the distal end 34 may be smooth, or provided with an annular groove 52 as shown to enable the outer portion of the bridge 42 to seat snugly therein. The annular groove 52 has two opposing annular shoulders 54 and 56 which abut against opposite sides of the outer portion of the bridge 42.

The interaction of the annular shoulders 48, 50, 54, and 56 and the bridge 42 enables the bridge 42 to function as a key to inhibit relative longitudinal movement of the electrode 23 and the sleeve 12. In this way, longitudinal shearing forces on the lead 10 that might otherwise urge the separation of the electrode 23 and the sleeve 12 are resisted by both the adhesive bond between the bridge 42 and the distal end 34, by the key-like functionality of the bridge 42, and possibly by any inherent adhesive properties exhibited by the sleeve 12 and the bridge 42, and/or any adhesive applied to the reduced diameter portion 30.

Figure 4:
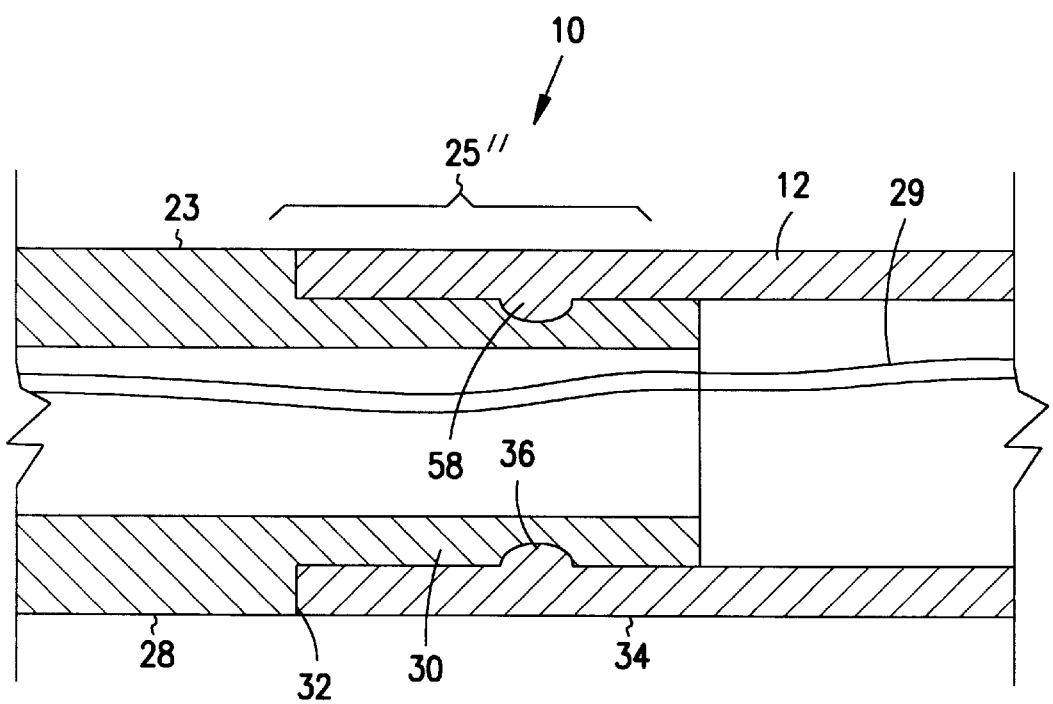
FIG. 4 is a cross-sectional view like FIG. 2 of another alternate embodiment of a cardiac lead joint assembly in accordance with the present invention.

FIG. 4 depicts another alternate embodiment of the joint assembly, now designated 25''. FIG. 4 shows the same general cross-section as depicted in FIGS. 2 and 3. The separately fabricated and installed bridges disclosed in the foregoing embodiments are replaced in this embodiment by an annular bridge 58 that is integrally molded into the interior surface of the distal end 34 of the sleeve 12. The bridge 58 is seated snugly in the annular groove 36. The distal end 34 is retained on the reduced diameter portion 30, at least partially, by interference. To provide this interference fit, the bridge 58 is fabricated with an unstretched inner diameter that is slightly smaller than the diameter of the reduced diameter portion 30 at the base of the annular groove 36.

Application of the distal end 34 to the reduced diameter portion 30 requires temporary stretching of the distal end 34 to an increased diameter so that the distal end 34 may be slipped over the reduced diameter portion 30 until the bridge 58 is seated in the annular groove 36. This stretching step may be accomplished by mechanical expansion or chemical swelling as described above. In addition to relying on interference to seat the bridge 58 in the annular groove 36, a suitable medical grade adhesive may be applied to the annular groove 36 and the outer surface of the reduced diameter portion 30 prior to seating the bridge 58.

The person of ordinary skill in the art will appreciate that the number, spacing, and particular configuration of the foregoing bridges as well as the configuration of the tubular members may be varied to satisfy particular design objectives. For example, a given joint assembly may be fabricated with a single rounded bridge, while another may be provided with a half dozen bridges, some with elliptical cross-sections, and some with rectangular cross-sections. It should also be appreciated that the tubular members may be structures other than conducting metallic electrodes or connectors. Non-metallic tubular structures, such as the individual branches in a branch assembly for a multiple-branch lead may be joined to polymeric sleeves using the techniques and structure describe above.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead joint assembly, comprising:
   a tubular member having an annular groove formed on the exterior surface thereof;
   a polymeric annular member disposed around the tubular member and seated in the annular groove; and
   a polymeric sleeve disposed over a portion of the tubular member and over the polymeric annular member, a portion of the polymeric sleeve proximate the polymeric annular member being diametrically stretched by the polymeric annular member, the polymeric sleeve being retained on the tubular member by interaction between the polymeric annular member and the polymeric sleeve.

2. The cardiac lead joint assembly of claim 1, comprising an adhesive applied between the polymeric annular member and the annular groove.

3. The cardiac lead joint assembly of claim 1, comprising an adhesive applied between the polymeric annular member and the polymeric sleeve.

4. The cardiac lead joint assembly of claim 1, wherein the annular groove and the polymeric annular member each have a rectangular cross-section.

5. The cardiac lead joint assembly of claim 1, wherein the tubular member comprises a metallic electrical connector for connecting the cardiac lead to a cardiac stimulator.

6. The cardiac lead joint assembly of claim 1, wherein the tubular member comprises a metallic electrode for establishing electrical connection between the lead and heart tissue.

7. The cardiac lead joint assembly of claim 1, wherein the polymeric annular member has an elliptical cross-section.

8. The cardiac lead joint assembly of claim 1, wherein the interior of the polymeric sleeve is bonded to the exterior of the tubular metallic member by an adhesive.

9. A cardiac lead joint assembly, comprising:
   a tubular metallic member having an annular groove formed in the exterior surface thereof; and
   a polymeric sleeve disposed over a portion of the tubular metallic member and the annular groove, the interior surface of the polymeric sleeve having an inwardly projecting annular member that is seated in the annular groove.

10. The cardiac lead joint assembly of claim 9, wherein the tubular member comprises a metallic electrical connector for connecting the cardiac lead to a cardiac stimulator.

11. The cardiac lead joint assembly of claim 9, where the tubular metallic member comprises a metallic electrode for establishing electrical connection between the lead and heart tissue.

12. The cardiac lead joint assembly of claim 9, wherein the interior of the polymeric sleeve is bonded to the exterior of the tubular metallic member by an adhesive.

13. A method of attaching a polymeric sleeve to a tubular metallic member of a cardiac lead, the tubular member having an annular groove formed in the exterior thereof, comprising the steps of:
   slipping a polymeric annular member over the tubular member and seating the polymeric annular member in the annular groove;
   applying an adhesive to the exterior of the polymeric annular member; and
   slipping the polymeric sleeve over the tubular member whereby the sleeve covers the polymeric annular member and whereby the adhesive bonds the exterior of polymeric annular member to the interior of the polymeric sleeve.

14. The method of claim 13, wherein the step of slipping the polymeric sleeve over the tubular member comprises temporarily expanding the polymeric sleeve prior to slipping the polymeric sleeve over the tubular member and contracting the polymeric sleeve after placement over the tubular member.

15. The method of claim 13, wherein the step of slipping the polymeric annular member over the tubular member includes applying adhesive to the annular groove.

16. The method of claim 13, wherein the step of slipping the polymeric annular member over the tubular member includes temporarily expanding the polymeric annular member, slipping the polymeric member over tubular member, seating the polymeric annular member in the groove, and contracting the polymeric annular member after placement over the tubular member.

17. A method of attaching a polymeric sleeve to a tubular metallic member of a cardiac lead, the tubular member having an annular groove formed in the exterior thereof, comprising the steps of:
   slipping a polymeric annular member over the tubular member and seating the polymeric annular member in the annular groove; and
   slipping the polymeric sleeve over the tubular member whereby the sleeve covers the polymeric annular member and whereby the exterior of polymeric annular member adheres to the interior of the polymeric sleeve.

18. The method of claim 17, comprising the step of applying an adhesive to the exterior of the polymeric annular member.

19. The method of claim 17, wherein the step of slipping the polymeric sleeve over the tubular member comprises temporarily expanding the polymeric sleeve prior to slipping the polymeric sleeve over the tubular member and contracting the polymeric sleeve after placement over the tubular member.

20. The method of claim 17, wherein the step of slipping the polymeric annular member over the tubular member includes applying adhesive to the annular groove.

21. The method of claim 17, wherein the step of slipping the polymeric annular member over the tubular member includes temporarily expanding the polymeric annular member, slipping the polymeric member over tubular member, seating the polymeric annular member in the groove, and contracting the polymeric annular member after placement over the tubular member.

22. A cardiac lead, comprising:
   a tubular electrode coupled to the distal end of a polymeric sleeve for passing electrical signals to and from heart tissue, the tubular electrode having an annular groove formed on the exterior surface thereof;
   a polymeric annular member disposed around the tubular electrode and seated in the annular groove; and
   a polymeric sleeve having a proximal end and a distal end disposed over a portion of the polymeric annular member and the tubular electrode and being secured to the polymeric annular member by an adhesive; and
   a tubular metallic connector coupled to the proximal end of the polymeric sleeve for connecting the lead to a cardiac stimulator.

23. A cardiac lead, comprising:
   a tubular electrode coupled to the distal end of a polymeric sleeve for passing electrical signals to and from heart tissue, the tubular electrode having an annular groove formed on the exterior surface thereof;
   a polymeric annular member disposed around the tubular electrode and seated in the annular groove, the polymeric annular member being composed of a first polymeric material;

a polymeric sleeve having a proximal end and a distal end disposed over a portion of the polymeric annular member and the tubular electrode, the polymeric sleeve being composed of a second polymeric material, the first and second polymeric materials exhibiting adhesive properties; and a tubular metallic connector coupled to the proximal end of the polymeric sleeve for connecting the lead to a cardiac stimulator.

24. The cardiac lead of claim 23, wherein the first and second polymeric materials comprise silicone.

25. A cardiac lead joint assembly, comprising:

a tubular metallic member having an annular groove formed in an exterior surface thereof, said annular groove having a rectangular cross-section; and a polymeric sleeve disposed over a portion of the tubular metallic member and the annular groove, the interior surface of the polymeric sleeve having an inwardly projecting annular member that is seated in the annular groove, said annular member having a rectangular cross section.

* * * * *

UNITED STATES PATENT AND TRADEMARK OFFICE
CERTIFICATE OF CORRECTION

PATENT NO. : 6,047,217
DATED : April 4, 2000
INVENTOR(S) : Uhrberg

It is certified that error appears in the above-identified patent and that said Letters Patent is hereby corrected as shown below:

Column 7,
Line 42, after "member", insert -- having an elliptical cross-section --.

Signed and Sealed this

Eleventh Day of September, 2001

Attest:

*Nicholas P. Godici*

NICHOLAS P. GODICI
*Attesting Officer*    *Acting Director of the United States Patent and Trademark Office*